United States Patent
Remer et al.

(10) Patent No.: US 10,933,113 B2
(45) Date of Patent: Mar. 2, 2021

(54) USE OF A COMPOUND, PHARMACEUTICAL COMPOSITION, AND THERAPEUTIC METHOD FOR THE TREATMENT OR PREVENTION OF CONVULSIONS

(71) Applicants: PROTEIMAX BIOTECNOLOGIA LTDA, São Paulo (BR); REMER CONSULTORES ASSESSORIA EMPRESARIAL LTDA, São Paulo (BR)

(72) Inventors: Ricardo Amaral Remer, Rio de Janeiro (BR); Andrea Sterman Heimann, São Paulo (BR)

(73) Assignee: PROTEIMAX BIOTECNOLOGIA LTD., Sao Paulo (BR)

( * ) Notice: Subject to any disclaimer, the term of this patent is extended or adjusted under 35 U.S.C. 154(b) by 0 days.

(21) Appl. No.: 16/341,856
(22) PCT Filed: Oct. 11, 2017
(86) PCT No.: PCT/BR2017/050313
§ 371 (c)(1),
(2) Date: Apr. 12, 2019
(87) PCT Pub. No.: WO2018/068119
PCT Pub. Date: Apr. 19, 2018

(65) Prior Publication Data
US 2019/0321438 A1  Oct. 24, 2019

(30) Foreign Application Priority Data
Oct. 13, 2016 (BR) .......................... 102016023848-0

(51) Int. Cl.
A61K 38/08 (2019.01)
A61P 25/08 (2006.01)
A61K 9/00 (2006.01)
A61K 38/10 (2006.01)

(52) U.S. Cl.
CPC ............ *A61K 38/08* (2013.01); *A61K 9/0053* (2013.01); *A61K 38/10* (2013.01); *A61P 25/08* (2018.01)

(58) Field of Classification Search
None
See application file for complete search history.

(56) References Cited

U.S. PATENT DOCUMENTS 9,796,760 B2   10/2017   Heimann

FOREIGN PATENT DOCUMENTS

| WO | 2011011847 | 3/2011 |
| WO | 2014/008567 A1 | 1/2014 |
| WO | 2014008567 | 1/2014 |

OTHER PUBLICATIONS

Rioli, Vanessa et al, "Novel natural peptide substrates for endopeptidase 24.15, neurolysin, and angiotensin-converting enzyme." J. Biol. Chem. (2003) 278(10) p. 8547-8555.*
Gholizadeh, Shervin et al, "Ultra-low dose cannabinoid antagonist am251 enhances cannabinoid anticonvulsant effects in the pentylenetetrazole-induced seizure in mice," Neuropharmacology (2007) 53 p. 763-770.*
Bass, Pat; "Differences between inhaled and oral corticosteroids for asthma." Verywell health webpage, https://www.verywellhealth.com/the-difference-between-inhaled-oral-corticosteroids-200612, downloaded Mar. 25, 2020.*
Dvoracsko, Szabolcs et al, "Investigation of receptor binding and functional characteristics of hemopressin(1-7)." Neuropeptides (Feb. 2016) 58 p. 15-22.*
Bomar, Martha G. and Galande, Amit K.; "Modulation of the cannabinoid receptors by hemopressin peptides." Life Sc. (2013) 92(8-9) p. 520-524.*
International Search Report and Written Opinion for PCT/BR2017/050313 transmitted on Jan. 25, 2018.
Gomes I et al. Hemoglobin-derived Peptides as Novel Type of Bioactive Signaling Molecules. AAPS J. 12(4): 2010.
Melisa J. Wallace et al. "The Endogenous Cannabinoid System Regulates Seizure Frequency and Duration in a Model of Temporal Lobe Epilepsy." Journal of Pharmacology and Experimental Therapeutic. 2003.
Melisa J. Wallace et al. "Assessment of the role of CB1 receptors in cannabinoid anticonvulsant effects." European Journal of Pharmacology 2001.
Gomes I et al. "Novel Endogenous Peptide Agonists of Cannabinoid receptors." FASEB J. 2009.
Couzin-Frankel, Jennifer. Epilepsy's next frontier. Science, vol. 366, Issue 6471, pp. 1300-1304 (2019).
Fogaca et al., Anxiogenic-like effects induced by hemopressin in rats. Pharmacology, Biochemistry and Behavior, 129, pp. 7-13 (2015).
Bauer et al., Identification and quantification of a new family of peptide endocannabinoids (Pepcans) showing negative allosteric modulation at CB1 receptors. The Journal of Biological Chemistry, vol. 287, No. 44, pp. 36944-36967 (2012).

* cited by examiner

*Primary Examiner* — Fred H Reynolds
(74) *Attorney, Agent, or Firm* — K&L Gates LLP

(57) ABSTRACT

The present invention relates to the fields of chemistry, pharmacy, biotechnology and medicine. More particularly, the present invention describes: the use of a peptide compound for preparing an anticonvulsant pharmaceutical composition; and a therapeutic method. The peptide compound of the claimed pharmaceutical composition binds to and/or modulates the activity of cannabinoid receptors (CB), particularly CB1 and/or CB2, and has proven to be extremely useful as an anticonvulsant. In one embodiment, the claimed pharmaceutical composition provides excellent anticonvulsant results when administered orally to a mammal, and, in addition to other advantages and technical effects, does not entail the drawbacks arising from the use of cannabinoid substances such as cannabidiol, and provides a stronger therapeutic effect in smaller dosages and with fewer side effects.

12 Claims, 3 Drawing Sheets

Specification includes a Sequence Listing.

SEQUENCE LISTING

```
<160> NUMBER OF SEQ ID NOS: 23

<210> SEQ ID NO 1
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 1

Val Asp Pro Val
1

<210> SEQ ID NO 2
<211> LENGTH: 5
<212> TYPE: PRT
<213> ORGANISM: Artificial Sequence
<220> FEATURE:
<223> OTHER INFORMATION: Synthesized Peptide

<400> SEQUENCE: 2

Arg Val Asp Pro Val
1               5

<210> SEQ ID NO 3
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 3

Asp Pro Val Asn Phe Lys Leu
1               5

<210> SEQ ID NO 4
<211> LENGTH: 7
<212> TYPE: PRT
<213> ORGANISM: Artificial Sequence
<220> FEATURE:
<223> OTHER INFORMATION: Synthesized Peptide
```

```
<400> SEQUENCE: 4

Asp Pro Val Asn Phe Lys Phe
1               5

<210> SEQ ID NO 5
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 5

Pro Val Asn Phe Lys Phe Leu
1               5

<210> SEQ ID NO 6
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 6

Pro Val Asn Phe Lys Leu Leu
1               5

<210> SEQ ID NO 7
<211> LENGTH: 8
<212> TYPE: PRT
<213> ORGANISM: Artificial Sequence
<220> FEATURE:
<223> OTHER INFORMATION: Synthesized Peptide

<400> SEQUENCE: 7

Pro Val Asn Phe Lys Phe Leu Ser
1               5

<210> SEQ ID NO 8
<211> LENGTH: 8
<212> TYPE: PRT
<213> ORGANISM: Artificial Sequence
<220> FEATURE:
<223> OTHER INFORMATION: Synthesized Peptide

<400> SEQUENCE: 8

Pro Val Asn Phe Lys Leu Leu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthesized Peptide

<400> SEQUENCE: 9

Pro Val Asn Phe Lys Phe Leu Ser His
1               5

<210> SEQ ID NO 10
<211> LENGTH: 9
<212> TYPE: PRT
<213> ORGANISM: Artificial Sequence
<220> FEATURE:
<223> OTHER INFORMATION: Synthesized Peptide
```

<400> SEQUENCE: 10

Pro Val Asn Phe Lys Leu Leu Ser His
1               5

<210> SEQ ID NO 11
<211> LENGTH: 11
<212> TYPE: PRT
<213> ORGANISM: Artificial Sequence
<220> FEATURE:
<223> OTHER INFORMATION: Synthesized Peptide

<400> SEQUENCE: 11

Val Asp Pro Val Asn Phe Lys Phe Leu Ser His
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthesized Peptide

<400> SEQUENCE: 12

Arg Val Asp Pro Val Asn Phe Lys Phe Leu Ser His
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthesized Peptide

<400> SEQUENCE: 13

Val Asp Pro Val Asn Phe Lys Phe Leu Ser His
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthesized Peptide

<400> SEQUENCE: 14

Arg Val Asp Pro Val Asn Phe Lys Leu Leu Ser His
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthesized Peptide

<400> SEQUENCE: 15

Val Asp Pro Val Asn Phe Lys Leu
1               5

<210> SEQ ID NO 16
<211> LENGTH: 8
<212> TYPE: PRT
<213> ORGANISM: Artificial Sequence
<220> FEATURE:
<223> OTHER INFORMATION: Synthesized Peptide

<400> SEQUENCE: 16

Val Asp Pro Val Asn Phe Lys Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Synthesized Peptide

<400> SEQUENCE: 17

Pro Val Asn Trp Lys Phe Leu Ser His
1               5

<210> SEQ ID NO 18
<211> LENGTH: 9
<212> TYPE: PRT
<213> ORGANISM: Artificial Sequence
<220> FEATURE:
<223> OTHER INFORMATION: Synthesized Peptide

<400> SEQUENCE: 18

Pro Val Asn Phe Lys Trp Leu Ser His
1               5

<210> SEQ ID NO 19
<211> LENGTH: 9
<212> TYPE: PRT
<213> ORGANISM: Artificial Sequence
<220> FEATURE:
<223> OTHER INFORMATION: Synthesized Peptide

<400> SEQUENCE: 19

Pro Val Asn Trp Lys Trp Leu Ser His
1               5

<210> SEQ ID NO 20
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 20

Pro Val Asn Trp Lys Phe Leu
1               5

<210> SEQ ID NO 21
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 21

Pro Val Asn Phe Lys Trp Leu
1               5

<210> SEQ ID NO 22
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 22

```
Pro Val Asn Trp Lys Trp Leu
1               5

<210> SEQ ID NO 23
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 23

Asp Ile Ile Ala Asp Asp Glu Pro Leu Thr
1               5                   10
```

USE OF A COMPOUND, PHARMACEUTICAL COMPOSITION, AND THERAPEUTIC METHOD FOR THE TREATMENT OR PREVENTION OF CONVULSIONS

RELATED APPLICATIONS

This application is a national stage entry under 35 U.S.C. § 371 of PCT/BR2017/050313, filed Oct. 11, 2017.

SEQUENCE LISTING

This application contains a sequence listing having the filename US-16341856-ST25.txt, which is 4,734 bytes in size, and was created on Mar. 25, 2020. The entire content of this sequence listing is herein incorporated by reference.

FIELD OF THE INVENTION

The present invention is in the fields of pharmacy, medicine, chemistry and biotechnology. More specifically, the present invention describes the use of hemopressin and variants with more than 7 amino acids to prepare an anticonvulsant pharmaceutical composition; an anticonvulsive pharmaceutical composition; and a therapeutic method. The anticonvulsive pharmaceutical composition of the invention may be administered orally. In one embodiment, oral administration of the composition of the invention showed significant and surprising results in the curative or prophylactic treatment of seizures. Test results show that administration of the compound of the invention provides for the interaction and/or modulation of muscarinic and/or cannabinoid (CB) receptor activity, especially CB1 and/or CB2, the pharmaceutical composition of the invention being a promising alternative to administration of cannabinoid compounds currently known as anticonvulsants, such as cannabidiol.

BACKGROUND OF THE INVENTION

The present invention describes for the first time the use of a peptidic compound including Hemopressin for the preparation of anticonvulsant pharmaceutical compositions.

Surprisingly, although the pharmaceutical composition of the invention comprises a peptide active, oral administration has provided brain effects in animals.

In various embodiments, in vivo tests with the pharmaceutical composition of the invention have shown surprising results regarding its anticonvulsant activity, and additionally provides the advantage of being a good candidate to substitute the known cannabinoid compounds for their acting as anticonvulsants, as is the case of Cannabidiol. Cannabidiol, despite its proven effects as an anticonvulsant, has been facing regulatory problems due to its origin, the *Cannabis sativa* plant. The present invention provides an additional therapeutic approach for patients suffering from seizures and having difficulty in obtaining drugs, being based on a peptide and not using derivatives of *Cannabis sativa*. In addition, the results showed that the anticonvulsant of the invention provides other surprising technical advantages in use, including greater therapeutic effect, oral use, lower dosage, less occurrence of side effects such as prostration and nasal bleeding, among other technical advantages.

Pilocarpine (commonly called "Pilo") is an alkaloid extracted from leaves of the *jaborandi* plant (*Pilocarpus jaborandi*), a plant used for centuries by the Tupi-Guarani Indians who inhabit Brazil and take advantage of their properties to produce sweat and saliva. Pilocarpine is a nonspecific muscarinic agonist, slowly degraded and without effects on nicotinic receptors and was introduced in clinical practice by the Brazilian physician Sifronio Coutinho, in 1874, through extracts from the *jaborandi* leaf to obtain a diaphoretic effect (sweat production) and silagogue (production of saliva).

Despite its pharmaceutical properties, pilocarpine at high concentrations induces the occurrence of convulsions, being used as an experimental model for both. Pilocarpine-induced seizures lead to neurotoxicity at the cellular level and may be related to increased cerebral oxidative stress and changes in the concentration of certain amino acids (Santos et al, 2011).

Administration of pilocarpine causes cholinergic changes capable of inducing status epilepticus (SE) associated with convulsive stereotyped movements. Pilo is able to induce status epilepticus both administered directly in the brain and intraperitoneally. This substance has been used in some experiments described in this patent application, its convulsive effects having been inhibited by the composition of the present invention.

Much of the understanding of the mechanisms of epilepsy comes from studies in experimental animal models, especially in rats and mice. In this context, the administration of pilocarpine in rodents mimics epilepsy (ELT) in humans and is generally referred to as the "pilocarpine model". This model was developed in 1983 by Turski et al. And is now one of the most widely used models of epilepsy, since its histological, biochemical, pharmacological, electrophysiological and behavioral characteristics (Turski et al., 1983) similarly reproduce those found in human carriers of ELT.

The pilocarpine model is also useful for evidence of changes in muscarinic receptors, such as salivation. Acetylcholine, through its muscarinic receptor (mAChRs) plays an important role in cognitive functions, such as learning and memory. mAChRs are receptors that form G protein-receptor complexes in the cell membranes of certain neurons and other cells. They play several roles, including acting as the ultimate end receptor stimulated by acetylcholine released from postganglionic fibers in the parasympathetic nervous system.

Muscarinic receptors are so called because they are more sensitive to muscarian than to nicotine. Its counterparts are nicotinic acetylcholine receptors (nAChRs), channels of receptor ions that are also important in the autonomic nervous system. Many drugs and other substances (eg, pilocarpine and scopolamine) manipulate these two distinct receptors acting as selective agonists or antagonists.

The mAChRs are among the most well characterized among the transmembrane receptors (7TM), being widely expressed in the central nervous system (CNS). Five mAChR subtypes were cloned (M1, M2, M3, M4 and M5) and are generally divided into two distinct classes based on signal transduction. mAChRs M1, M3 and M5 are subtypes that signal through Gq/11 proteins and activate phospholipase-C and mobilize intracellular calcium. The mAChRs M2 and M4, however, predominate through Gi/o proteins inhibiting adenylate cyclase and reducing the intracellular concentration of cAMP. The predominant mAChR in the CNS is the M1 subtype, which is located in the cortex, hippocampus, striatum and thalamus, where it is found post-synaptic. M2 mAChRs are located predominantly in the brainstem and thalamus, but also in the cortex, hippocampus and striatum, where they control the release of acetylcholine. mAChRs of M3 and M5 are expressed at much lower levels than M1 or M3 mAChRs in the CNS, but M3 mAChRs are found in the cortex and hippocampus, while M5 mAChRs have a very discrete location in the substantia nigra. M4 mAChRs are found in many regions of the brain, including the cortex and hippocampus, but are more prominent in the striatum, where they are thought to play a role in the control of dopamine release and modulate locomotor activity.

The test results presented in the present patent application indicate that the composition of the invention interacts with cannabinoid and/or muscarinic receptor receptors. The results show that the compound of the invention is anticonvulsive.

Experimental data indicate that the active compound of the invention interacts with and/or modulates the activity of cannabinoid (CB) receptors. The cannabinoid system, which comprises the CB1 and CB2 receptors and their endogenous ligands, acts on several metabolic functions, including control of food intake and energy metabolism, among others. Cannabinoid receptors are widely expressed in the brain, including cortex, hippocampus, amygdala, pituitary, and hypothalamus. CB receptors, particularly CB1, have already been identified in numerous peripheral organs and tissues, including the thyroid gland, adrenal gland, reproductive organs, adipose tissue, liver, muscle, and gastrointestinal tract.

Various compounds have already been detected in the art having modulation activity of these receptors. Among these, some target the development of drugs for weight reduction and thinning of the waist, such as rimonabant. However, this compound was subsequently associated with increased occurrence of psychiatric diseases in humans and was removed from the world market.

Prior art searches have disclosed documents only partially relevant to the present invention. Such documents will be described below, and are set forth herein solely for the purpose of serving as a basis for the state of the art, since none of them anticipates or even suggests any of the objects of the present invention.

US 2007/213302 discloses CB1 receptor interacting compounds, consisting of pyrazoles and their pharmaceutically acceptable salts which act as antagonists or inverse agonists of the CB1 receptor. The present invention differs from said document, among other reasons, because it has a pharmaceutical composition which does not comprise pyrazoles or salts thereof, the results of which are surprising in inhibiting the occurrence of seizures, facts not described or suggested in said document.

Some studies presented by one of the present inventors in Novel Peptide Substrates for Endopeptidase 24.15 Neurolysin and Angiotensin Converting Enzyme (Vanessa Rioli, Fabio C. Gozzo, Andrea S. Heimann, Alessandra Linardi, Joseph E. Krieger, Claudio S. Shida, Paulo C. Almeida, Stephen Hyslop, Marcos N. Eberlin, Emer S. Ferro, Mar. 7, 2003) demonstrate an effective technique of "screening" of new peptides. The present invention differs from this document, among other reasons, for presenting a new therapeutic approach to seizures, the results of which were surprising.

WO 2014/008567, of one of the present inventors, discloses compounds and compositions useful for treating metabolic disorders comprising obesity, diabetes, systemic arterial hypertension (or disease, condition related and/or associated comorbidities); prevention of overweight; regulation of appetite; induction of satiety; prevention of weight gain after successful weight loss; increased energy consumption; aesthetic weight reduction; or bulimia. No report or suggestion of use of the compound of the invention as an anticonvulsant is made in said document, not least because this approach was not imagined by the inventors nor was it obvious from the state of the art.

WO 2011/011847 discloses the use of hemopressin for the treatment of obesity in a subject and further discloses that hemopressin is a compound that binds effectively to the CB1 receptor. The present invention differs from said document, among other reasons, by providing a composition for another therapeutic use, in addition to revealing for the first time the surprising anticonvulsant activity.

WO 2013/021196 discloses the use of hemopressin as an agent that interferes with the differentiation of oligodentrites and is useful as an anti-demyelinating agent. The present invention differs from said document, among other reasons, because it reveals another use. The results of tests performed by the present inventors have been surprising in regard to inhibition of the occurrence of seizures, which is neither described nor suggested in said document.

Other references of scientific literature circumscribing the invention, but without anticipating or suggesting it, include the following documents.

ASPRONI, B. et al. Novel pyrrolocycloalkylpyrazole analogues as CB1 ligands. Chemical Biology and Drug Design, p. 1-13, 2017.

HILDEBRANDT, A. K. et al. Efficient computation of root mean square deviations under rigid transformations. Journal of Computational Chemistry, v. 35, p. 765-771, 2014.

HUA T, et al. Crystal structure of the human cannabinoid receptor CB1. Cell, v. 167, p. 750-762, 2016.

MAIOROV, V. N.; CRIPPEN, G. M. Significance of root-mean-square deviation in comparing three-dimensional structures of globular proteins. Journal of Molecular Biology, v. 235, p. 625-634, 1994.

MORGAN, C. A.; HURLEY, T. D. Characterization of two distinct structural classes of selective aldehyde dehydrogenase 1A1 inhibitors. Journal of Medicinal Chemistry, v. 58, p. 1964-1975, 2015.

PERTWEE, R. G. The diverse CB1 and CB2 receptor pharmacology of three plant cannabinoids: A9-tetrahydrocannabinol, cannabidiol and L\9-tetrahydrocannabivarin. British Journal of Pharmacology, v. 153, p. 199-215, 2008.

RAMACHANDRAN, G. N.; RAMAKRISHNAN, C.; SASISEKHARAN, V. Stereochemistry of polypeptide chain configurations. Journal of Molecular Biology, v. 7, p. 95-99, 1963.

SANTOS, P. S. et al. Efeitos do acido lipoico nas concentracoes de glutamate e taurina no hipocampo de ratos apps convulsoes induzidas por pilocarpina, Arq. Neuro-Psiquiatr. [online]. 2011, vol. 69, n. 2b, pp. 360-364.

MUNRO et al. Nature 365:61-65, 1993.

RINALDI-CARMONA M. et al. J. Pharmacol, Exp. Ther. 278:871-878, 1996.

Langmead CJ1, Watson J, Reavill C. Muscarinic acetylcholine receptors as CNS drug targets. Pharmacol Ther. 2008 February; 117(2):232-43. Epub 2007 Dec. 20.

From the reviewed literature; no document was found anticipating or suggesting the teachings of the present invention, let alone their surprising technical effects, so that the solution proposed here, in the eyes of the inventors, has novelty and inventive activity over the state of the art.

SUMMARY OF THE INVENTION

The present invention addresses a major problem known in the art by providing: the use of a peptidic compound to prepare anticonvulsant medicament; an anticonvulsive pharmaceutical composition; a therapeutic method. The pharmaceutical composition of the invention does not have the drawbacks arising from the use of the cannabinoid substances, such as prostration and/or nasal bleeding, among others.

One of the objects of the present invention is the use of a peptide compound of at least 7 aminoacids of formula:

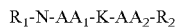

where:
$AA_1$ is an aminoacid selected from the group consisting of F, W, L, I, V, P, G;
$AA_2$ is an aminoacid selected from the group consisting of F, W, L, I, V; P, G;
$R_1$ is the dipeptide PV, the tripeptide DPV, the tetrapeptide VDPV (SEQ ID NO:1), or the pentapeptide RVDPV (SEQ ID NO:2); and
$R_2$ is the aminoacid L, the dipeptide LH, or the tripeptide LSH, and/or modified or cyclic forms thereof, amide-, methyl-, or PEG-versions thereof, its salts; and/or combinations thereof, for the preparation of a medicament for curative or prophylactic treatment of convulsions in a mammal.

In one embodiment, $AA_1$ and/or $AA_2$ is F, W or L.

It is a further object of the invention to provide an alternative compound to cannabidiol and which provides advantages in the production, handling, use and safety and can replace it in all or almost all the applications already described therefor.

It is another object of the invention to provide a compound useful for modulating muscarinic receptors and/or the cannabinoid system, either by modulating the CB1 receptor, the CB2 receptor, both concurrently by modulating the binding or action of other substances which interact in the cannabinoid system by the modulation of proteases or peptidases that lead to the generation or degradation of active peptides in the cannabinoid system, or combinations thereof.

Another object of the invention is a pharmaceutical composition for the curative or prophylactic treatment of seizures in a mammal, said composition comprising a pharmaceutically acceptable carrier; and, as active principle, the compound described above.

Embodiments of the pharmaceutical composition of the invention include one or more of the peptides selected from the group consisting of: DPVNFKL (SEQ ID NO:3), DPVNFKF (SEQ ID NO:4), PVNFKFL (SEQ ID NO:5), PVNFKLL (SEQ ID NO:6), PVNFKFLS (SEQ ID NO:7), PVNFKLLS (SEQ ID NO:8), PVNFKFLSH (SEQ ID NO:9), PVNFKLLSH (SEQ ID NO:10), VDPVNFKFLSH (SEQ ID NO:11), RVDPVNFKFLSH (SEQ ID NO:12), VDPVNFKFLSH (SEQ ID NO:13), RVDPVNFKLLSH (SEQ ID NO:14), VDPVNFKL (SEQ ID NO:15), VDPVNFKF (SEQ ID NO:16), PVNWKFLSH (SEQ ID NO:17), PVNFKWLSH (SEQ ID NO:18), PVNWKWLSH (SEQ ID NO:19), PVNWKFL (SEQ ID NO:20), PVNFKWL (SEQ ID NO:21), PVNWKWL (SEQ ID NO:22), as well as modified, cyclic forms thereof, amidated, methylated, PEGylated versions; their salts; or combinations thereof.

In one embodiment, the anticonvulsive pharmaceutical composition of the invention comprises the nonapeptide PVNFKFLSH (SEQ ID NO:9), the nonapeptide PVNFKLLSH (SEQ ID NO:10), or combinations thereof.

In one embodiment, the pharmaceutical composition is in the form of a tablet, gel, oral liquid or syrup, capsule, suppository, injectable solution or inhalable or adhesive forms, and may optionally comprise other active principles.

Administration of the pharmaceutical composition of the invention to an animal provides important and surprising technical advantages, including: anticonvulsant activity; enables oral administration in animals; does not have or entails the drawbacks arising from the production, storage, transport and use of cannabinoid substances, in addition to providing additional advantages in the preparation of therapeutic products for mammals in their administration and/or effects.

Another object of the present invention is a curative or prophylactic therapeutic method of seizures comprising administering to an animal the compound as described above.

These and other objects of the present application will be immediately appreciated by those skilled in the art and by companies having interests in the art and will be described in sufficient detail for their reproduction in the following description.

BRIEF DESCRIPTION OF THE FIGURES

The following detailed description and the accompanying figures illustrate the main features and embodiments of the present invention, set forth in greater detail to provide further support to the person skilled in the art, and so that the latter may understand and reproduce the inventive concept of the invention in any of its embodiments. Such details or figures are not to be construed as limiting and serve only to illustrate some of the embodiments of the present invention.

FIG. 1 shows the results of convulsive tests with the pilocarpine model, indicating the survival time of the animals after administration of pilocarpine and the test compounds in the assay. The data on the peptide of the invention PVNFKFLSH (SEQ ID NO:9) (or Hp) 1000 μg/kg shown is of only one animal that died. Although data between control, Hp 600 μg/kg and DIIADDEPLT (SEQ ID NO:23) 1000 μg/kg (also referred to in this application as PEP-19) are not statistically significant, the Hp 1000 μg/kg data shown in the graph is just an animal that died. The remaining animals in the group treated with the anticonvulsant composition of the invention, totaling 4, remained alive for more than a week, while all the others died in less than 20 minutes. Consequently, the mean survival time for this group is significantly different and higher than the others when Hp 1000 μg/kg is administered.

FIG. 2 shows the results of tests with the anticonvulsant composition of the invention PVNFKFLSH (SEQ ID NO:9) (or Hp) on the pilocarpine model, indicating the number of dead animals in the group with n=5. The asterisk (*) $P<0.001$ vs Control, Hp 600 μg/kg, Hp 1000 μg/kg, DIIADDEPLT (SEQ ID NO:23) 1000 μg/kg (Pep-19).

FIG. 3 shows the results of tests with the anticonvulsant composition of the invention comprising the peptide PVNFKFLSH (SEQ ID NO:9) (or Hp) in the pilocarpine model, with the survival/death profile of the animals being indicated. In A) the survival profile of the animals administered the control (saline only) is shown: In B) the survival profile of the animals given the DIIADDEPLT (SEQ ID NO:23) peptide 1000 μg/kg (Pep-19) is shown; In C) the survival profile of the animals to which the anticonvulsant composition of the invention was administered comprising PVNFKFLSH (SEQ ID NO:9) (or Hp) 600 μg/kg; In D) the survival profile of the animals to which the peptide of the invention PVNFKLLSH (SEQ ID NO:10) (or Hp) was administered 1000 μg/kg: In E) all profiles are shown in a single graph.

FIG. 4 shows the test results of the anticonvulsant composition of the invention comprising PVNFKFLSH (SEQ ID NO:9) (or Hp) in the pilocarpine model, the time for the occurrence of the first salivation being indicated. The asterisk (*) indicates P<0.01 vs DIIADDEPLT (SEQ ID NO:23) (1000 µg/kg, also referred to herein as PEP19 and used as another control).

DETAILED DESCRIPTION OF THE INVENTION

Figure 1:
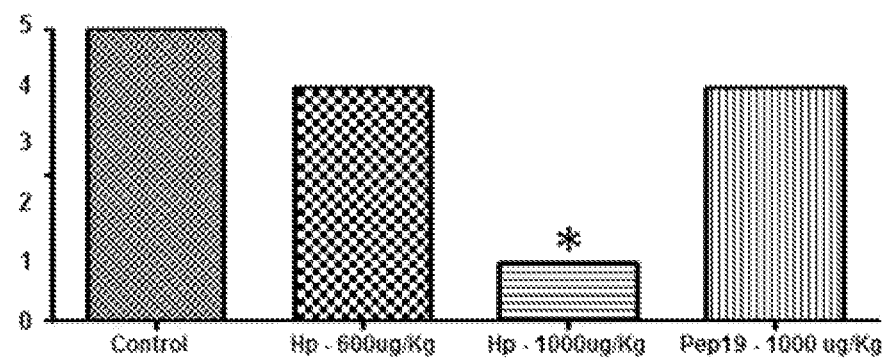

In the present invention, there is provided the use of the peptidic compound described below for the preparation of a medicament for the curative or prophylactic treatment of seizures. Peptides of the present invention include hemopressin, which for the first time surprisingly showed significant and long-lasting anticonvulsant effects.

In various embodiments, in vivo tests with the compound of the invention have demonstrated surprising results regarding its anticonvulsant activity, further providing the advantage of being a good candidate to substitute for the cannabinoid compounds known to act as anticonvulsants, as is the case with Cannabidiol. Cannabidiol, despite its proven effects as an anticonvulsant, has been facing regulatory problems due to its origin, the *Cannabis sativa* plant. The present invention provides an additional therapeutic approach for patients suffering from seizures and having difficulty obtaining drugs, being based on a peptide, ie, does not use derivatives of *Cannabis sativa*. In addition, the results showed that the anticonvulsant pharmaceutical composition of the invention provides other surprising technical advantages in use, including greater therapeutic effect, oral use, lower dosage, less occurrence of side effects such as prostration and nasal bleeding, among other technical advantages.

The inventive concept common to the various objects of the invention is the use of a compound for the preparation of an anticonvulsant pharmaceutical composition, said compound comprising at least 7 amino acids of the formula:

$R_1$-N-$AA_1$-K-$AA_2$-$R_2$ where:
$AA_1$ is an aminoacid selected from the group consisting of F, W, L, I, V, P, G;
$AA_2$ is an aminoacid selected from the group consisting of F, W, L, I, V, P, G;
$R_1$ is the dipeptide PV, the tripeptide DPV, the tetrapeptide VDPV (SEQ ID NO:1), or the pentapeptide RVDPV (SEQ ID NO:2); and
$R_2$ is the aminoacid L, the dipeptide LH, or the tripeptide LSH, and/or modified or cyclic forms thereof, amide-, methyl-, or PEG-versions thereof, its salts; and/or combinations thereof,
for the preparation of a medicament for curative or prophylactic treatment of convulsions in a mammal.

Compound of Pharmaceutical Interest

In the context of the present application, "compound of pharmaceutical interest" means any molecular entity comprising the compound described as an inventive concept common to the present application, also including molecular entities obtained by chemical derivatization thereof, with the inclusion of other functional groups, linear or branched side chains, alteration of hydrophilicity or hydrophobicity, among others, provided that they comprise as nucleus the entity $R_1$-N-$AA_1$-K-$AA_2$-$R_2$ as defined above, except for natural and already known entities.

Pharmaceutical Composition

In the context of the present patent application, "pharmaceutical composition" is to be understood as any and all compositions containing an active principle, for prophylactic, palliative and/or curative purposes, acting in a manner to maintain and/or restore the homeostasis, and may be administered orally, topically, parenterally, enterally and/or intrathecally.

Pharmaceutically Acceptable Formulation

In the context of the present application, a "pharmaceutically acceptable formulation" is understood to mean a formulation containing pharmaceutically acceptable excipients and carriers well known to those skilled in the art, such as the development of convenient doses and treatments for use in particular compositions which can be described in a number of treatment regimens, including oral, parenteral, intravenous, intranasal, intravitreal and intramuscular, intracerebral, intracerebroventricular and intraocular and their administration and/or formulation.

Modified Peptide

In the context of the present application, "modified peptide" is to be understood as a non-naturally occurring, artificially modified or synthesized peptide, including cyclized, amidated, methylated, PEGylated forms, or salt forms thereof, as well as a peptide comprising one or more unnatural amino acid, such as d-aminoacid forms. The peptidic compound may be pegylated using techniques known to those skilled in the art, such as, for example, pegylation with reagents containing the succinimidyl group, which preferentially react with primary amines present in the N-terminal region of the peptide.

Cyclic or Circular Peptide

In the context of the present application, "cyclic, cyclized or circular peptide" is to be understood as a peptide which has a covalent bond between the two ends of a linear peptide molecule by any method known in the art, particularly by the activity of enzymes. The cyclic peptide can be used instead of the linear peptide because it is more difficult to be degraded, since its ends or zones of attack by hydrolyzing enzymes are not as exposed as in a linear peptide.

Agonist

In the context of the present application, "agonist" is to be understood as a drug, drug, hormone, neurotransmitter or other signaling molecule which forms a complex with a receptor site, thereby triggering an active response of a cell.

Inverse Agonist/Antagonist

In the context of the present application, "inverse agonist or antagonist" shall be understood as agent(s) (for example, drugs, drugs, hormones or enzymes) which bind(s) to agonist receptors and produce(s) pharmacological effects opposite to those of the agonists, such that the action of one partially or totally inhibits the effect of the other. Particularly, a compound is an inverse agonist when it acts in the presence of an agonist, but reducing its activity; an antagonist is a compound that will totally block the activity of the agonist.

Equivalent Dose in Humans

In the present invention, the concept of "equivalent dose in humans" is the dose at which, in humans, the same magnitude of effects is expected in animals at a given dose, as set forth in "Guidance for Industry Estimating the Maximum Safe Starting Dose in Initial Clinical Trials for Therapeutics in Adult Healthy Volunteers" published by the US Department of Health and Human Services Food and Drug Administration Center for Drug Evaluation and Research (CDER), July 2005 Pharmacology and Toxicology. In said guide, the conversion of the observed dose in animals (mg/kg) to Equivalent Dose in Humans (mg/kg) entails dividing the result obtained in rats by 6.2 and the result obtained in mice by 12.3. These values are applicable to a human of 60 kg standard weight. For other species or for weights outside the standard weight ranges, the Dose Equivalent in Humans (DEH) can be calculated by the formula: DEH=dose in animal in mg/kg×(animal weight in kg/human weight in kg)$^{0.33}$. This Guidance considers a safety range of 10 times the concentration limits tested to be adequate.

Modulating the CB Receptor Function or the Cannabinoid System

In the context of the present patent application, it is meant to "modulate the CB receptor function" as an interaction that results in the alteration of the biochemical activity of the CB receptor, particularly CB1 or CB2. It is understood that the change is positive when an antagonist or inverse agonist effect occurs at CB receptors and that the change is negative when an agonist effect occurs at CB receptors. The tests presented in the present patent application suggest that the compound of the invention interacts with and/or modulates the CB1 receptor and/or the CB2 receptor, probably as an allosteric modulator of CB1 and/or CB2 receptor. Thus the compound of the invention is useful for modulating the cannabinoid system, either by modulating the CB1 receptor, the CB2 receptor, both concomitantly, by modulating the binding or action of other substances interacting in the cannabinoid system, by modulating proteases or peptidases which lead to the generation or degradation of active peptides in the cannabinoid system, or combinations thereof.

Modulating the Function of Muscarinic Receptors

In the context of the present application, the term "modulating the muscarinic receptor function" should be understood as an interaction leading to neuronal changes, including muscannic acetylcholine receptor (mAChRs), which plays an important role in cognitive functions, such as such as learning and memory, control of dopamine release, modulation of locomotor activity, its modulation being also useful in the control of Alzheimer's disease and/or control of addiction or addiction to drugs of abuse. It is understood that the change is positive when an antagonist or inverse agonist effect occurs at muscarinic receptors and that the change is negative when an agonist effect occurs at muscarinic receptors. The tests presented in the present patent application suggest that the compound of the invention interacts with and/or modulates muscarinic receptors.

While in this invention it is shown that said compound binds and/or modulates cannabinoid receptors, the surprising pharmaceutical action of the invention may be linked to action on CB1 and/or CB2 and/or muscarinic or possibly be linked to uptake modulation adenosine, GGPR55, PPARγ receptors, intracellular calcium level, or combinations thereof.

The present invention is also defined by the following clauses.

Use of the compound described above for the preparation of a medicament for the curative or prophylactic treatment of seizures in a mammal.

Use as described above wherein $AA_1$ or $AA_2$ is F, W or L.

Use as described above wherein said compound is selected from the group consisting of: DPVNFKL (SEQ ID NO:3), DPVNFKF (SEQ ID NO:4), PVNFKFL (SEQ ID NO:5), PVNFKLL (SEQ ID NO:6), PVNFKFLS (SEQ ID NO:7), PVNFKLLS (SEQ ID NO:8), PVNFKFLSH (SEQ ID NO:9), PVNFKLLSH (SEQ ID NO:10), VDPVNFKFLSH (SEQ ID NO:11), RVDPVNFKFLSH (SEQ ID NO:12), VDPVNFKFLSH (SEQ ID NO:13), RVDPVNFKLLSH (SEQ ID NO:14), VDPVNFKL (SEQ ID NO:15), VDPVNFKF (SEQ ID NO:16), PVNWKFLSH (SEQ ID NO:17), PVNFKWLSH (SEQ ID NO:18), PVNWKWLSH (SEQ ID NO:19), PVNWKFL (SEQ ID NO:20), PVNFKWL (SEQ ID NO:21), PVNWKWL (SEQ ID NO:22), as well as modified, cyclic forms thereof, amidated, methylated, PEGylated versions; their salts; or combinations thereof.

Use as described above wherein said compound is the nonapeptide PVNFKFLSH (SEQ ID NO:9), the nonapeptide PVNFKLLSH (SEQ ID NO:10), or combinations thereof.

A pharmaceutical composition for the curative or prophylactic treatment of seizures in a mammal comprising a pharmaceutically acceptable carrier; and, as active principle, the compound described above Pharmaceutical composition as described above in the form of a tablet, gel, oral liquid or syrup, capsule, suppository, injectable solution, inhalable form or in adhesive.

A curative or prophylactic therapeutic method of seizures comprising administering to an animal the compound described above.

In vivo tests in mammals showed excellent therapeutic effect at low dosages. The anticonvulsant effect is evidenced by the absence or decrease of symptoms associated with the administration of pilocarpine.

In addition, test results have shown that the composition of the invention provides surprising technical advantages in use, including greater therapeutic effect, viability of oral use, lack of use of carrier oil (which in many cases causes side effects), lower dosage and non-occurrence of side effects such as prostration and nasal bleeding, among others.

In the present invention, the use of the compound as described above for the preparation of a medicament for the curative or prophylactic treatment of seizures is provided for the first time.

In addition, as will be demonstrated in the following examples, the pharmaceutical composition of the invention provides for obtaining a medicament orally administrable to a mammal. The test results revealed significant brain action, suggesting that the active element crosses the blood-brain barrier. Thus, the results show/support the use of the compound of the invention regardless of whether the compound of the invention is the active which acts directly on the target, ie, does not degrade during oral ingestion, or the compound is a precursor which, upon modification post-administration chemistry, acts on the target—in this case, being characterized as pro-drug. This feature of providing important effects even by oral administration is particularly desirable, since the natural enzymes of a mammal in general degrade peptides and proteins while in the digestive tract and rarely a drug with a peptidic active is shown to be viable. However, surprisingly, the compound of the invention—even when administered orally—provides strong therapeutic action, in this case even more surprisingly, acting in the brain.

Therefore, regardless of the mechanism of action, which is not the subject of the present application, the fact that the oral administration of the pharmaceutical composition of the invention has provided important action and anticonvulsant, clearly shows the surprising magnitude and relevance of the resolved technical problems.

The present application discloses a pharmaceutical composition comprising the compound described above. Said pharmaceutical composition also comprises a pharmaceutically acceptable carrier, optionally also comprising other pharmaceutically acceptable actives and/or salts thereof. The compound of the invention is one or an active component of the pharmaceutical composition of the invention, which is administered in the form of a tablet, gel, capsule, oral liquid or syrup, a suppository, an injectable solution or other suitable forms of administration for pharmaceutical and medical purposes.

The following examples are only intended to exemplify some of the various ways in which the invention may be embodied, however, without limiting the scope thereof.

In some instances, the anticonvulsive effects of the composition of the invention have been evaluated in vivo upon oral administration to animals. The pharmaceutical composition of the invention was administered to mammals (*Mus musculus* or mouse) with oral dose of treatment, as compared to other compounds or to saline control. In these experiments, the test compounds were administered orally 10 minutes prior to the (intraperitoneal) administration of pilocarpine. Pilocarpine hydrochloride (320 mg/kg, Merck), dissolved in 0.9% sterile saline, was given intraperitoneally for induction of SE (status epilepticus) (Turski et al., 1983). In the Turski model, the neurotoxic effects begin about 15-25 minutes after the injection of Pilo, with the occurrence of motor and limbic seizures, the animals evolving to a state of continuous (clonic) seizures that characterize SE Sanabria and Cavalheiro, 2000).

EXAMPLES

Example 1. Use of the Compound $R_1$-N-$AA_1$-K-$AA_2$-$R_2$ for the Preparation of an Anticonvulsant Pharmaceutical Composition In this embodiment, the compound R1-N-AA1-K-AA2-R2 is the peptide PVNFKFLSH (SEQ ID NO:9), also known as hemopressin or Hp, which has been synthesized by chemical synthesis. Said peptide has been used in the preparation of an oral liquid anticonvulsive pharmaceutical composition comprising 1.5.times.10-4 Molar of said peptide and a pharmaceutically acceptable carrier. In this embodiment, said carrier is saline, the pharmaceutical composition being a solution for oral use, Said composition was used for oral in vivo administration to mammals according to examples 1 and 3 below.

In other embodiments, the pharmaceutical composition is in the form of a tablet, gel, oral liquid or syrup, a capsule, a suppository, an injectable solution or inhalable or adhesive forms, optionally comprising other active principles Example 2. Anticonvulsant Pharmaceutical Composition Comprising the Compound PVNFKFLSH (SEQ ID NO:9) (Hp)—Results of In Vivo Tests In this embodiment, the anticonvulsant effect of the composition of the invention prepared according to example 1 was evaluated by prior administration of the inventive composition and subsequent administration of pilocarpine to animals. Administration of pilocarpine leads to severe brain damage, neurotoxicity, and usually culminates in the death of animals. This substance was used in the experiments described below but its harmful neuronal/encephalic effects were inhibited by the prior administration of the composition of the present invention: the vast majority of the animals subjected to these experiments had no brain injury related symptoms and survived without apparent damage, in contrast to groups of animals treated with other known substances.

The composition of the invention prepared according to Example 1 was pre-administered to the animals.

FIG. 1 shows the survival time results of the animals after administration of pilocarpine and test compounds in the assay. The data on the anticonvulsant composition of the invention comprising PVNFKFLSH (SEQ ID NO:9) (or Hp) 1000 µg/kg shown is only one animal that died. Although the data between control, Hp 600 µg/kg and DIIADDEPLT (SEQ ID NO:23) 1000 µg/kg are not statistically significant, the data for Hp 1000 µg/kg shown in the graph is only one animal that died. The remaining animals in the group treated with the anticonvulsant composition of the invention, in a total of 4, remained alive for more than a week, while all the others died in less than 20 minutes. Consequently, the mean survival time for this group is significantly different and higher than the others when Hp 1000 µg/kg is administered.

Figure 2:
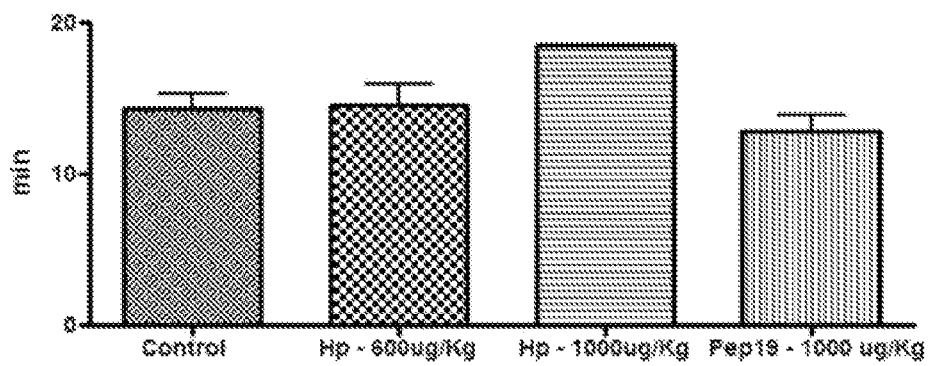

FIG. 2 shows the results of seizure tests with the anticonvulsant composition of the invention comprising the PVNFKFLSH (SEQ ID NO:9) (or Hp) peptide in the pilocarpine model, indicating the number of animals dead in the group with n=5. The asterisk (*) $P<0.001$ vs Control, Hp 600 µg/kg, Hp 1000 µg/kg, DIIADDEPLT (SEQ ID NO:23) 1000 µg/kg (Pep-19).

Figure 3:
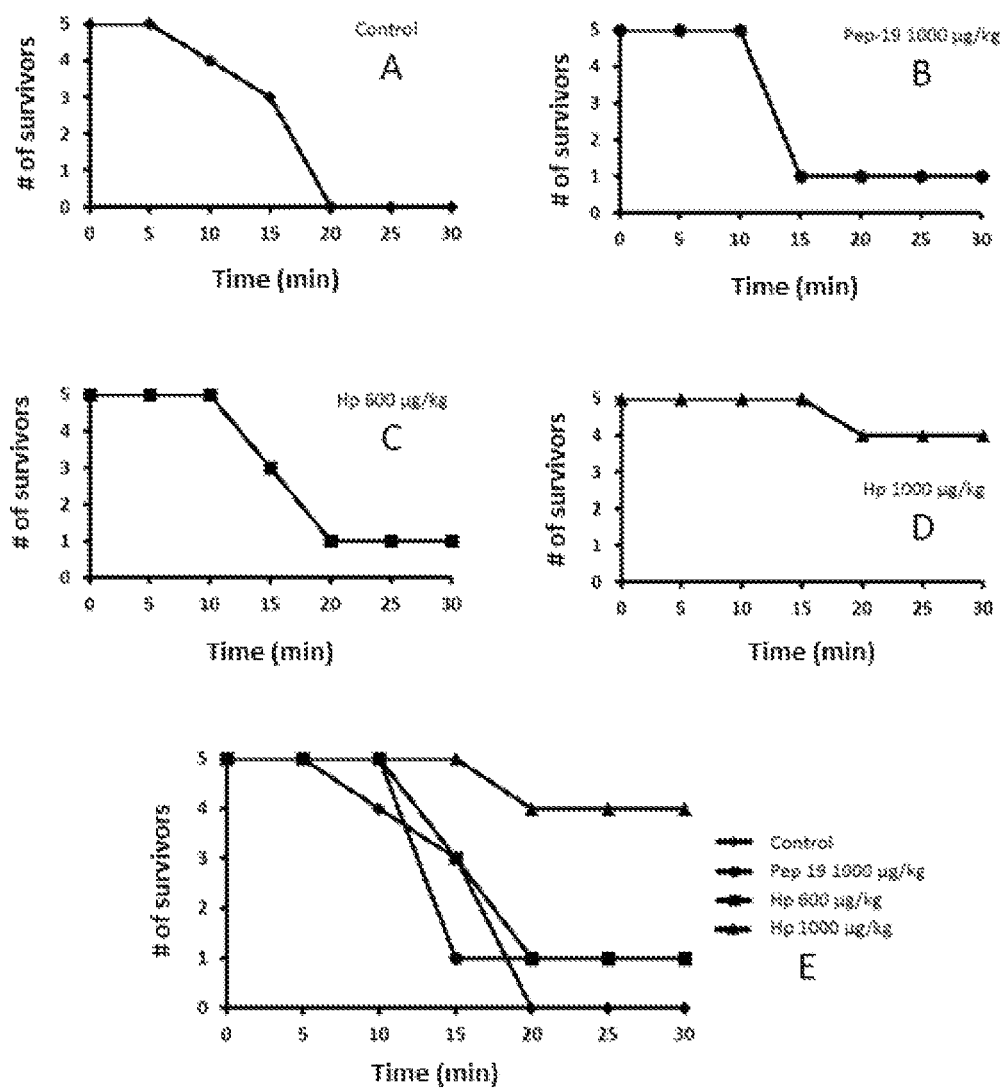

FIG. 3 shows the results of seizure tests with the anticonvulsant composition of the invention comprising the PVNFKFLSH (SEQ ID NO:9) (or Hp) peptide in the pilocarpine model, indicating the survival/death profile of the animals. In A) the survival profile of the animals administered the control (saline only) is shown; In B) the survival profile of the animals given the DIIADDEPLT (SEQ ID NO:23) peptide 1000 µg/kg (Pep-19) is shown; In C) the survival profile of the animals given the PVNFKFLSH (SEQ ID NO:9) (or Hp) peptide 600 µg/kg was shown; In D) the survival profile of the animals given the PVNFKFLSH (SEQ ID NO:9) (or Hp) peptide 1000 µg/kg; In E) all profiles are shown in a single graph.

Among other technical advantages, the occurrence of typical side effects of other anticonvulsants, such as prostration and nasal bleeding, has not been observed.

Example 3. Anticonvulsant Pharmaceutical Composition Comprising the Compound PVNFKFLSH (SEQ ID NO:9) (Hp)—Results of In Vivo Tests In this embodiment of the invention, the anticonvulsive composition of the invention in which the peptide R1-N-AA1-K-AA2-R2 is the nonapeptide PVNFKFLSH (SEQ ID NO:9), was used for administration to mammals in the tests described below.

Figure 4:
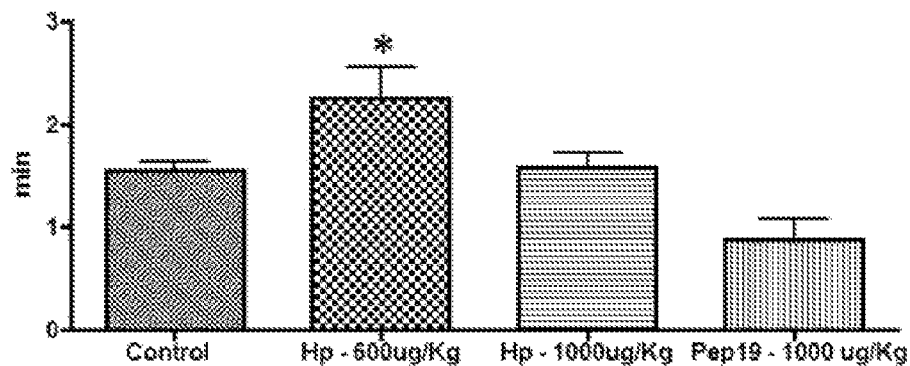

FIG. 4 shows the results of the pilocarpine model, indicating the time for the first salivation to occur. The asterisk (*) indicates $P<0.01$ vs Pep19 1000 µg/kg.

On the one hand, salivation induced by the administration of pilocarpine is indicative of changes in muscarinic receptors. Accordingly, the substantial change in the time profile for the occurrence of the first salivation observed with prior administration of the compound of the invention suggests modulation, either directly or indirectly, of muscarinic receptors.

In addition, the results of FIG. 4 clearly show that oral administration of the compound of the present invention provides activity modulating the time of occurrence of the first salivation.

Figure 5:
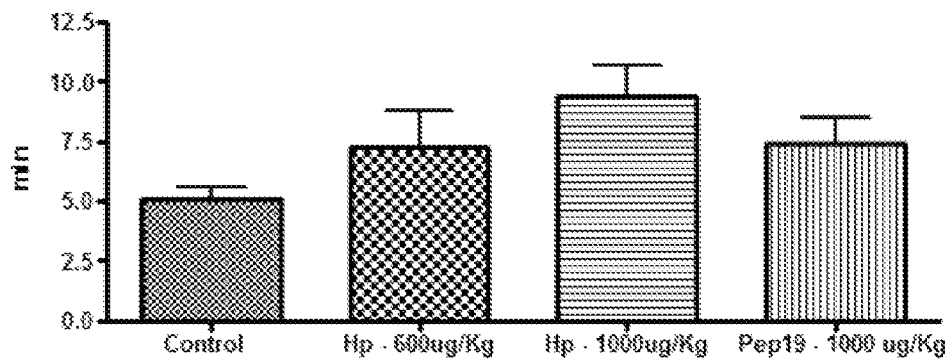
FIG. 5 shows the test results of the anticonvulsant composition of the invention comprising PVNFKFLSH (SEQ ID NO:9) (or Hp) in the pilocarpine model, the time for the occurrence of the first signal convulsive state signal being indicated.

FIG. 5 shows the results of tests with the pilocarpine model, indicating the time for the occurrence of the first convulsive signal.

Figure 6:
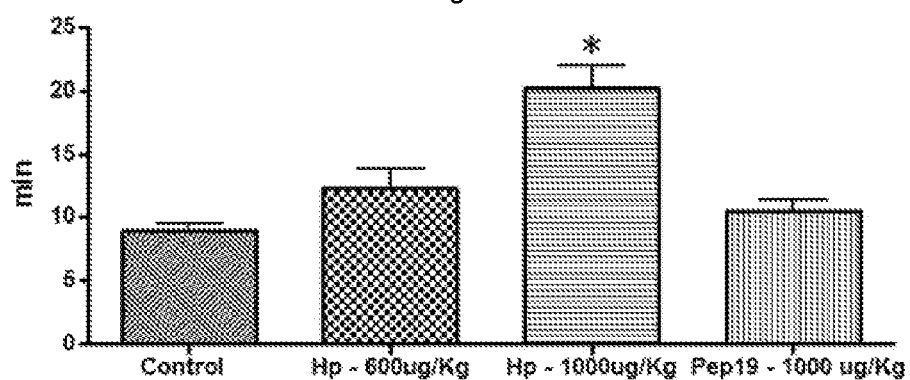
FIG. 6 shows the test results of the anticonvulsant composition of the invention comprising PVNFKFLSH (SEQ ID NO:9) (or Hp) in the pilocarpine model, indicating the time for the occurrence of the first seizure. The asterisk (*) indicates P<0.001 vs Control, Hp (600 µg/kg), peptide DIIADDEPLT (SEQ ID NO:23) (1000 µg/kg, used as another control).

FIG. 6 shows the results of tests with the pilocarpine model, indicating the time for the occurrence of the first seizure. The asterisk (*) indicates P<0.001 vs Control, Hp 600 µg/kg, Pep19 1000 µg/kg.

The results of the tests performed in examples 2 and 3 above show significant and significant in vivo results in dosage ranges of the order of 600 to 1000 µg of compound of the invention per kg of animal. Considering the tests in mice and the conversion to the Human Equivalent Dose mentioned above, effects of the same magnitude are expected in humans in the dosage range of 48 to 80 µg of compound of the invention per kg of human and, considering the applicable safety ranges, concentrations between 4.8 to 800 µg/kg for human administration are considered in the present invention.

The inventive concept herein disclosed and exemplified in one or more ways was treated as an industrial secret and was not previously disclosed until the filing of this patent application. This industrial secret is immaterial asset of the applicant. The possible future publication of the patent application does not in itself constitute authorization for use by third parties, serving only to: (i) provide scientific knowledge to third parties of the existence of said industrial secret on the date of filing; (ii) provide unequivocal indication of its holder; and (iii) stimulate the development of new improvements based on the disclosed concept, in order to avoid reinvestment in the development of the same asset already held by the applicant.

It is immediately noted that any commercial use requires authorization from the holder and that unauthorized use imposes penalties provided for by Law. In this context, it is first clarified that from the disclosure of the present inventive concept, those skilled in the art may consider other embodiments of the invention not identical to those merely exemplified above, but that in the hypothesis of commercial use such forms may be considered to be within the scope of the appended claims.

The invention claimed is:

1. A method of treating convulsions in a subject in need thereof, comprising administering to the subject a pharmaceutical composition comprising a pharmaceutically acceptable carrier and an active principle, wherein the active principle consists essentially of a compound having the formula:

PVNFKFLSH (SEQ ID NO:9) or PVNFKLLSH (SEQ ID NO:10)

or a salt thereof, wherein one or more of the amino acids of the compound may be a D-amino acid, the compound may be a cyclic peptide, the compound may be amidated, the compound may be methylated, the compound may be pegylated, or a combination thereof.

2. The method of claim 1, wherein the compound is formulated in a tablet, gel, liquid, syrup, or capsule form.

3. The method of claim 1, wherein the pharmaceutical composition is formulated in an oral or inhalable form.

4. The method of claim 1, wherein one or more of the amino acids of the compound is a D-amino acid, the compound is a cyclic peptide, the compound is amidated, the compound is methylated, the compound is pegylated, or a combination thereof.

5. The method of claim 4, wherein the compound is formulated in a tablet, gel, liquid, syrup, or capsule form.

6. The method of claim 4, wherein the pharmaceutical composition is formulated in an oral or inhalable form.

7. The method of claim 1, wherein the compound is administered in a dosage range of 4.8 to 800 µg of the compound per kg of the subject.

8. The method of claim 2, wherein the compound is administered in a dosage range of 4.8 to 800 µg of the compound per kg of the subject.

9. The method of claim 3, wherein the compound is administered in a dosage range of 4.8 to 800 µg of the compound per kg of the subject.

10. The method of claim 4, wherein the compound is administered in a dosage range of 4.8 to 800 µg of the compound per kg of the subject.

11. The method of claim 5, wherein the compound is administered in a dosage range of 4.8 to 800 µg of the compound per kg of the subject.

12. The method of claim 6, wherein the compound is administered in a dosage range of 4.8 to 800 µg of the compound per kg of the subject.

* * * * *